United States Patent [19]

Green et al.

[11] Patent Number: 5,304,143
[45] Date of Patent: Apr. 19, 1994

[54] VALVE SYSTEM FOR INTRODUCING OBJECTS INTO ANATOMICAL BODY PORTIONS

[75] Inventors: David T. Green, Westport; Henry Bolanos, East Norwalk, both of Conn.

[73] Assignee: United States Surgical Corporation, Norwalk, Conn.

[21] Appl. No.: 992,143

[22] Filed: Dec. 17, 1992

Related U.S. Application Data

[63] Continuation of Ser. No. 711,756, Jun. 7, 1991, Pat. No. 5,180,373.

[51] Int. Cl.$^5$ .............................................. A61M 8/00
[52] U.S. Cl. ..................................... 604/167; 604/156
[58] Field of Search ................................ 604/167, 256

[56] References Cited

U.S. PATENT DOCUMENTS

| | | |
|---|---|---|
| 2,797,837 | 7/1957 | Roberts . |
| 3,197,173 | 7/1965 | Taubenheim . |
| 3,875,938 | 4/1975 | Mellor . |
| 3,970,089 | 7/1976 | Saice . |
| 3,977,400 | 8/1976 | Moorehead . |
| 4,000,739 | 1/1977 | Stevens . |
| 4,177,814 | 12/1979 | Knepshield et al. . |
| 4,233,982 | 11/1980 | Bauer et al. . |
| 4,240,411 | 12/1980 | Hosono . |
| 4,243,034 | 1/1981 | Brandt . |
| 4,338,934 | 7/1982 | Spademan . |
| 4,379,458 | 4/1983 | Bauer et al. . |
| 4,424,833 | 1/1984 | Spector et al. . |
| 4,430,081 | 2/1984 | Timmermans . |
| 4,512,766 | 4/1985 | Vailancourt . |
| 4,531,937 | 7/1985 | Yates . |
| 4,535,773 | 8/1985 | Yoon . |
| 4,580,573 | 4/1986 | Quinn . |
| 4,610,665 | 9/1986 | Matsumoto et al. . |
| 4,610,674 | 9/1986 | Suzuki et al. . |
| 4,611,785 | 9/1986 | Steer . |
| 4,626,245 | 12/1986 | Weinstein . |
| 4,629,450 | 12/1986 | Suzuki et al. . |
| 4,634,432 | 1/1987 | Kocak . |
| 4,654,030 | 3/1987 | Moll et al. . |
| 4,655,752 | 4/1987 | Honkanen et al. . |
| 4,673,393 | 6/1987 | Suzuki et al. . |

(List continued on next page.)

FOREIGN PATENT DOCUMENTS

| | | |
|---|---|---|
| 29864 | 6/1981 | European Pat. Off. . |
| 054728 | 6/1982 | European Pat. Off. . |
| 0150666 | 8/1985 | European Pat. Off. . |
| 0323018 | 7/1989 | European Pat. Off. . |
| 0344907 | 12/1989 | European Pat. Off. . |
| 0350291 | 1/1990 | European Pat. Off. . |
| 0370720 | 5/1990 | European Pat. Off. . |
| 2845643 | 4/1980 | Fed. Rep. of Germany . |
| 3042229 | 5/1982 | Fed. Rep. of Germany . |
| 3242870 | 6/1983 | Fed. Rep. of Germany . |
| 1199498 | 6/1970 | United Kingdom . |
| 2019219 | 10/1979 | United Kingdom . |
| 2063679 | 6/1981 | United Kingdom . |

*Primary Examiner*—Paul J. Hirsch

[57] ABSTRACT

A valve assembly adapted for introduction of an elongated object into a patient's body having a first valve formed of a resilient material and defining an aperture for reception of the object, the aperture being configured and dimensioned such that insertion of the object into the aperture will cause the resilient material defining the aperture to resiliently engage the outer surface of the object in a fluid tight manner. A second valve is positioned adjacent and distal of the first valve in general alignment therewith, whereby the second valve defines an aperture in general alignment with the aperture of the first valve, and is formed of a flexible material at least in the region defining the aperture. A pair of manually operable clamps are provided to selectively permit the aperture of the second valve to be opened or closed so as to permit entry of the object such that the object first passes through the first valve and then the second valve prior to entry into the patient's body.

37 Claims, 4 Drawing Sheets

U.S. PATENT DOCUMENTS

| | | |
|---|---|---|
| 4,759,751 | 7/1988 | Gabel et al. . |
| 4,798,594 | 1/1989 | Hillstead . |
| 4,813,938 | 3/1989 | Raulerson . |
| 4,842,591 | 6/1989 | Luther . |
| 4,857,062 | 8/1989 | Russell . |
| 4,874,377 | 10/1989 | Newgard et al. . |
| 4,895,346 | 1/1990 | Steigerwald . |
| 4,909,798 | 3/1990 | Fleischhacker et al. . |
| 4,917,668 | 4/1990 | Haindl . |
| 4,929,235 | 5/1990 | Merry et al. . |
| 4,935,010 | 6/1990 | Cox et al. . |
| 4,960,259 | 10/1990 | Sunnaväder et al. . |
| 4,960,412 | 10/1990 | Fink . |
| 4,966,588 | 10/1990 | Rayman et al. . |
| 4,978,341 | 12/1990 | Wiederhauser . |
| 5,000,745 | 3/1991 | Guest et al. . |
| 5,006,114 | 4/1991 | Rogers et al. . |
| 5,009,391 | 4/1991 | Steigerwald . |
| 5,053,014 | 10/1991 | Van Heugten ............... 604/167 |
| 5,098,393 | 3/1992 | Amplatz et al. . |
| 5,112,321 | 5/1992 | Hiltebrandt ............... 604/167 |
| 5,127,626 | 7/1992 | Hilal et al. . |
| 5,197,955 | 3/1993 | Stephens et al. ............... 604/256 |

VALVE SYSTEM FOR INTRODUCING OBJECTS INTO ANATOMICAL BODY PORTIONS

This is a continuation of copending application Ser. No. 07/711,756 filed Jun. 7, 1991 now U.S. Pat. No. 5,120,373.

BACKGROUND OF THE INVENTION

1. Field Of The Invention

This invention relates to valve systems of the type adapted to allow the introduction of a surgical instrument into a patient's body. In particular, the invention is applicable to a cannula assembly and the like wherein a cannula extends from a valve assembly and is intended for insertion into a patient's body and an instrument is inserted into the patient's body through the cannula.

2. Background Of The Prior Art

In laparoscopic procedures surgery is performed in the interior of the abdomen through a small incision; in endoscopic procedures surgery is performed in any hollow viscus of the body through narrow endoscopic tubes or cannula inserted through a small entrance incision in the skin. Laparoscopic and endoscopic procedures generally require that any instrumentation inserted into the body be sealed, i.e. provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system comprised of a cannula assembly and a trocar. A cannula assembly is formed of a cannula attached to a valve assembly which is adapted to maintain a seal across the opening of the valve assembly. Since the cannula is in direct communication with the internal portion of the valve assembly, insertion of the cannula into an opening in the patient's body so as to reach the inner abdominal cavity should be adapted to maintain a fluid tight interface between the abdominal cavity and the outside atmosphere.

Since surgical procedures in the abdominal cavity of the body require insufflating gases to raise the cavity wall away from vital organs, the procedure is usually initiated by use of a Verres needle through which a gas is introduced into the body cavity. Thereafter, a trocar, which is a sharp pointed instrument, is inserted into a cannula assembly and used to puncture the peritoneum, i.e. the inner lining of the abdominal cavity wall. The gas provides a slight pressure which raises the wall surface of the peritoneum away from the vital organs thereby avoiding unnecessary contact with the organs by the instruments inserted into the cannula. This procedure also provides the surgeon with an adequate region in which to operate. Laparoscopic or endoscopic surgical instruments may then be inserted through the cannula to perform surgery within the abdominal cavity or other body portion. The cannula is also utilized for introducing tubes into the body as for drainage purposes or the like.

In view of the need to maintain the atmospheric integrity of the inner area of the cavity, a valve assembly which permits introduction of a trocar or any surgical instrument and which permits selective communication of the inner atmosphere of the cavity with the outside atmosphere is desirable. In this regard, there have been a number of attempts in the prior art to provide such atmospheric integrity.

One form of cannula assembly includes a valve assembly which includes a flapper valve which is pivotally mounted within the valve assembly and is automatically opened by the trocar or other object when it is inserted into the proximal end of the valve assembly. See, e.g., U.S. Pat. No. 4,943,280 to Lander.

U.S. Pat. No. 4,960,412 relates to a catheter introducing system which includes a valve assembly having dual flexible resilient gaskets which permit introduction of a catheter by providing dual openings which are dimensioned to contact a catheter tube introduced into the unit. Introduction of the tube is accomplished by introducing the tube into the openings of the gaskets. A first valve prevents or minimizes the flow of blood from the valve assembly unit when the catheter tube is absent and the second valve prevents or minimizes the flow of blood from the valve assembly when the catheter tube is present.

Another valve includes finger operated levers for controlling an inner valve formed of a plurality of radially movable members which join in adjacent relation to close the valve opening and which separate to permit entry of an element into the valve opening. The members are concentrically positioned and arranged to block the opening when the levers are at rest and to open in a manner to form a substantially circular passage-way when the levers are squeezed toward each other against the bias of a spring positioned therebetween.

Although attempts have been somewhat successful in providing a valve assembly which maintains the integrity of the atmospheric interface between the inlet of the valve assembly and the atmosphere outside the valve assembly, none have provided the degree of control to the user whereby opening adapted to facilitate the introduction of an instrument into the human body can be controlled selectively, opened or closed, in sequence and in a manner which positively retains the desired interface between the two atmospheres as may be required by the operator. The present invention provides a valve assembly which may be incorporated into a cannula assembly or utilized in combination with any type of tubular member for introduction into the body of a patient while permitting introduction of instruments into the body. At all times, the surgeon maintains control over the interface between the atmospheres within and without the patient's body. Moreover, the present invention makes it possible to introduce instruments of varying sizes into the body and insures the maintenance of a gas seal despite instrument manipulation therethrough.

SUMMARY OF THE INVENTION

A valve assembly adapted for introduction of an elongated object into a patient's body is provided which comprises first valve means formed of a resilient material and defining an aperture for reception of the object, the aperture being configured and dimensioned such that insertion of the object into the aperture will cause the resilient material defining the aperture to resiliently engage the outer surface of the object in a substantially fluid tight manner. Second valve means is positioned adjacent the first valve means in general alignment therewith, the second valve means defining an aperture in general alignment with the aperture of the first valve means and being formed of a flexible material at least in the region defining the aperture. Means is provided to selectively permit the aperture of the second valve means to be opened or closed so as to permit entry of the object.

Preferably, the valve assembly comprises valve body means which defines proximal inlet and distal outlet openings. The first valve means is formed of an elastomeric resilient material and extends across the proximal inlet opening of the valve body, and defines an aperture configured and dimensioned for reception of the object in a manner such that resilient material surrounding the aperture engages the surface of the object to provide a substantially fluid tight seal which prevents passage of fluids past the interface. The second valve means is positioned adjacent and distally of the first valve means and both valve means extend across the proximal inlet opening of the valve body. The second valve means includes an aperture defined at least in part by flexible elastomeric material in general alignment with the aperture of the first valve means and of dimension sufficient to permit passage of the object after the object is passed through the first valve means. Means is provided to bias the flexible material defining the aperture of the second valve means to a configuration whereby the aperture is closed to form a fluid tight seal prior to inserting the object therethrough, and means is provided to open the aperture of the second valve means to permit passage of the object therethrough after the object is passed through the first valve means. Preferably, means to open the aperture of the second valve means is manually operable.

The objects contemplated are surgical instruments such as clip appliers, dissectors, graspers, laser and electrocautery devices, drainage or fluid introduction tubes or the like. The first valve means is positioned across the proximal opening of the valve body and the second valve means is positioned adjacent the first valve means and distally thereof. Further, the first and second valve means are preferably formed integrally of a flexible elastomeric resilient material, with the first valve means connected to the second valve means at the proximal ends thereof, the first valve means being positioned at least partially within the second valve means. The first and second valve means are joined at their proximal ends and are attached to the valve body across the proximal opening. The valve body includes a neck which extends distally of the distal end thereof, the neck defining an opening communicating with the interior of the valve body means. Further, the distally extending neck of the valve body is adapted to receive a tubular cannula such that the cannula extends distally of the valve body.

The second valve means comprises an elastomeric generally cylindrically shaped member which is preferably connected integrally at the proximal end thereof to the proximal end of the first valve means and is open at the distal end. The distal opening of the second valve means is capable of being closed by collapsing the distal end until the half portions thereof resiliently contact each other to form a substantial fluid tight seal. The distal end of the second valve means is biased toward the closed fluid tight position by a clamp which is positioned and adapted to bias the open end of the second valve means toward the collapsed configuration. The clamp comprises a pair of clamp blades, each blade connected to a portion of the distal open end of the second valve means. The clamp blades are each biased toward each other to close the distal opening of the second valve means by a respective torsion spring mounted within the valve body. Each clamp blade is connected to a pivotal arm and each pivotal arm is biased toward the position corresponding to the closed position of the second valve means. The pivotal arms are mounted for pivotal movement toward the valve-open position by reception into an aperture of at least one slidable pin. The pins are movable manually by engagement by the user's fingers.

The first and second valve means are preferably attached to and supported by an annular ring which includes a plurality of elongated fingers which extend distally therefrom and are positioned within the first valve means in contact with the inner surface thereof. The fingers provide an interface between the first valve means and objects inserted therein and assist in spreading the opening of the first valve means for entry of the instrument. Further, the fingers distribute the force over the inner surface of the first valve means.

Each slidable pin has a frusto-conical shaped tip adjacent each pivot arm for engagement with the respective pivot arm when the pins are moved toward each other by manual action of the user. Further, the valve body is preferably a two piece valve housing assembled at a medial interface and constructed of a relatively rigid plastic material such as polycarbonate, polyethylene or the like.

In a preferred embodiment, a cannula and trocar assembly is provided for puncturing a body wall of a patient for the introduction of elongated objects as surgical instruments or the like into the body of the patient while maintaining a substantial fluid tight seal between internal body portions and the outside atmosphere at all times prior to and after insertion of the object. The valve housing has an inlet opening at the proximal end and an outlet opening at the distal end, the distal end opening having a tubular cannula extending distally therefrom. A trocar is positioned within the valve housing and the cannula for puncturing the body wall. Thereafter, the trocar is removed and elongated objects such as surgical instruments or the like may be introduced into the patient's body through the valve assembly and cannula as described hereinabove.

In the preferred embodiment the first and second valves are molded integrally of synthetic or natural rubber and are connected at a common proximal end which defines the proximal opening. The first valve means has a generally conical shape and is positioned within the second valve means in a generally concentric fashion. The valve means are mounted onto a support ring which is used to mount the valve means to an annular portion within the valve housing.

A method is provided for selectively sealing a valve assembly for communication with inner portions of a patient's body while permitting introduction of an elongated instrument therethrough, the valve assembly having a proximal inlet opening and a distal outlet opening, comprising providing first valve means comprised of resilient material defining an opening which permits entry therethrough by the instrument while resiliently contacting the outer surface, providing second valve means distal of the first valve means, and selectively controlling the open and closed condition of the second valve means to permit passage of the instrument after entry through the first valve means.

DETAILED DESCRIPTION OF THE PREFERRED EMBODIMENTS

The present invention contemplates introduction into a patient's body of all types of surgical instruments including clip appliers, lasers, photographic devices, tubes, etc. All such objects are referred to herein as "instruments".

Figure 1:
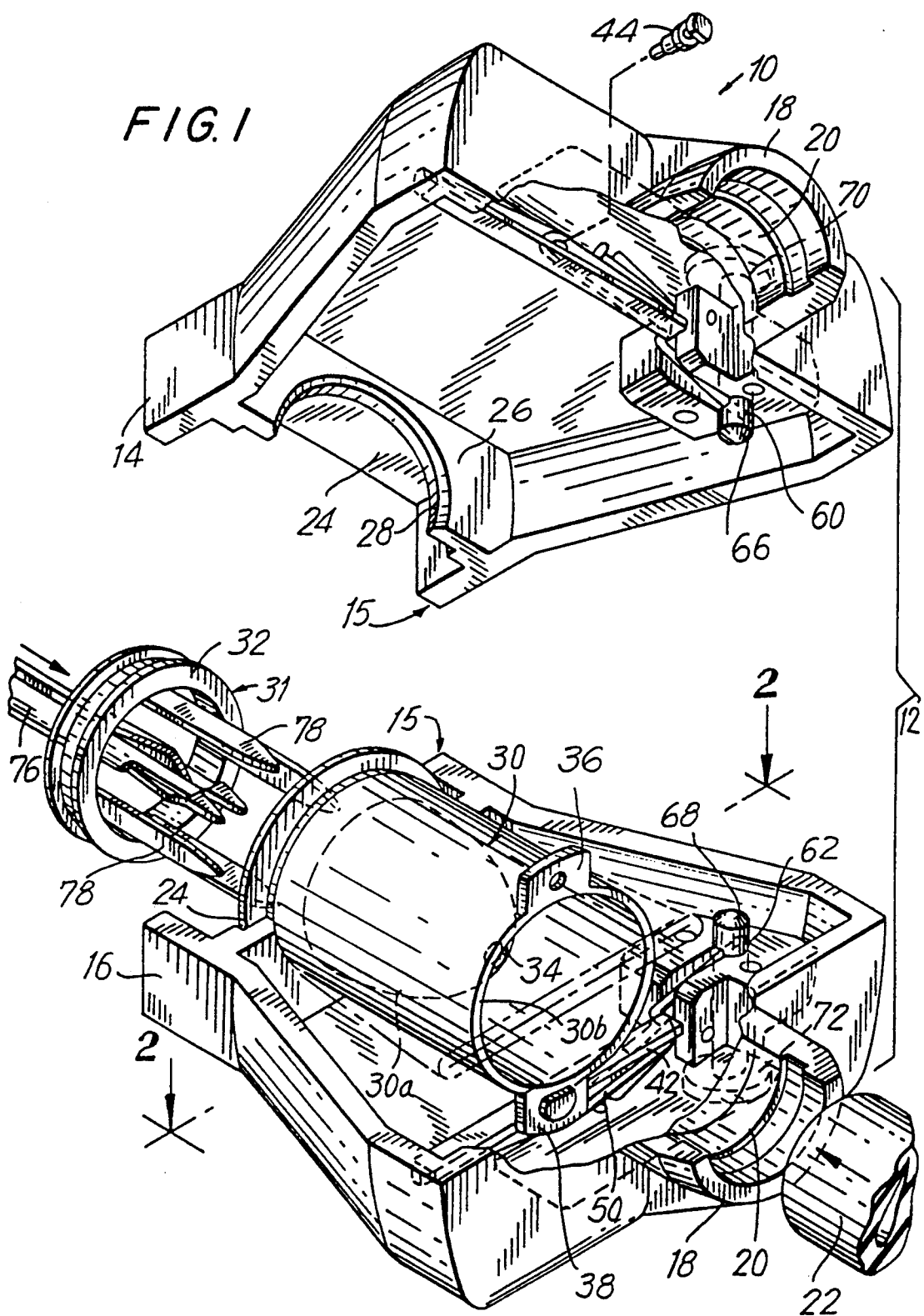
FIG. 1 is an exploded perspective view of a cannula assembly illustrating the valve assembly constructed according to the present invention.
Figure 2:
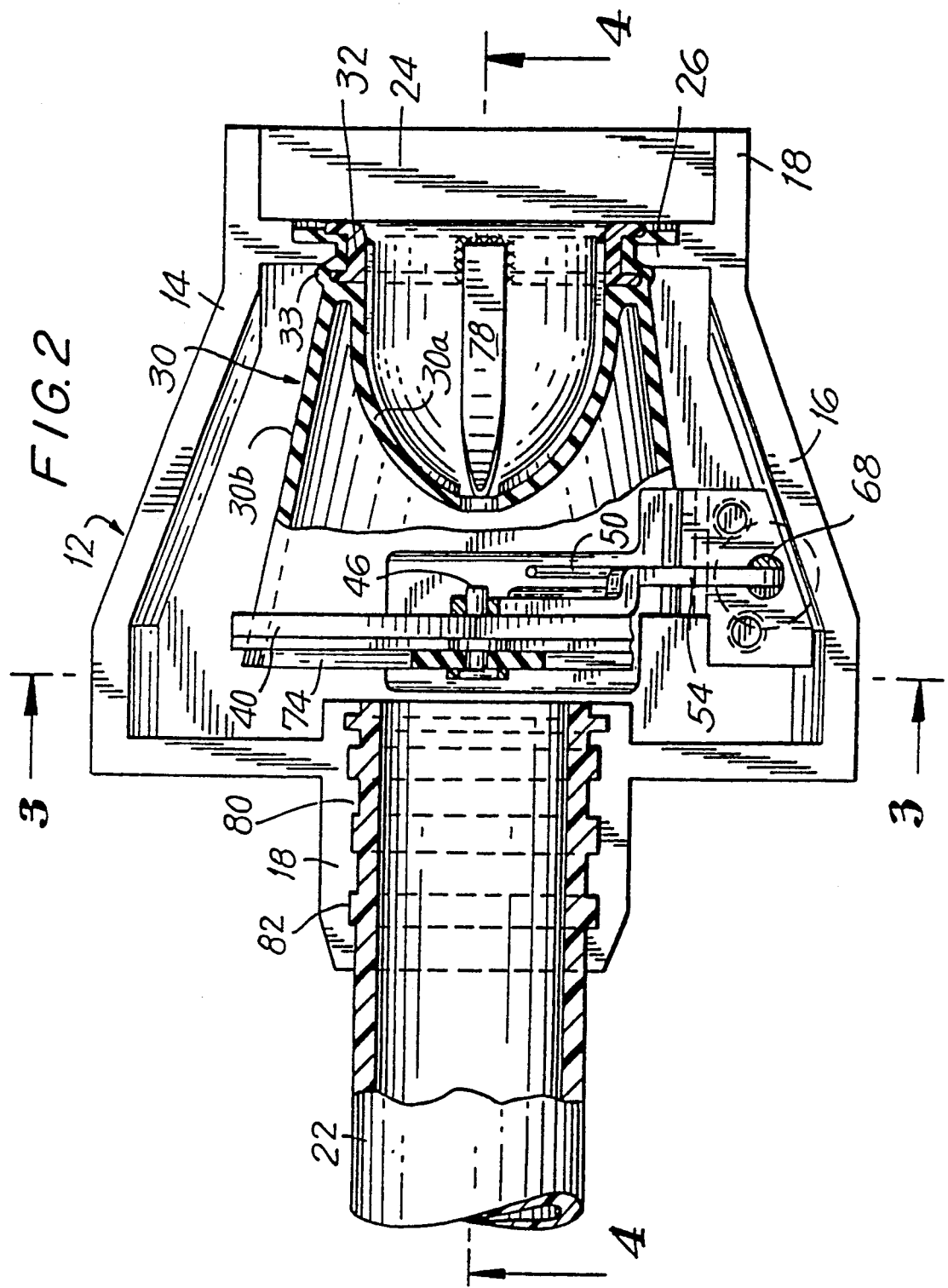
FIG. 2 is a view of the lower housing half section shown in FIG. 1 with portions of the inner valve and cannula cut away for illustration purposes.

Referring initially to FIGS. 1 and 2, a cannula assembly 10 is illustrated having the novel valve assembly 12 constructed according to the present invention. Valve assembly 12 includes a valve housing 15 formed of upper housing half section 14 and lower housing half section 16 shown separated in FIG. 1 for convenience of illustration.

The housing half sections 14,16 are formed of a suitable desirable plastic material such as polycarbonate, polyethylene or the like. One preferred material is LEXAN brand polycarbonate manufactured and marketed by General Electric Company, Pittsfield, Mass. The housing half sections 14,16 are normally attached along the seam by suitable attachment techniques such as adhesive, ultrasonic welding, or the like.

The valve housing 15 includes neck 18 at the distal end having an aperture 20 dimensioned for reception of an appropriate sheath tube such as cannula 22 to form the cannula assembly 10. The proximal end of valve housing 15 includes inlet opening 24 which includes annular partition 26 for supporting a dual diaphragm as will be described.

Referring now to FIG. 2, the lower housing half section 16 is shown with the upper housing half section 14 removed, so as to illustrate the novel inner valve mechanism of the present invention. The valve mechanism is shown partially cut away and in cross section. Dual flexible elastomeric sealing diaphragm 30 extends across the aperture 20 of housing 15 as shown. The diaphragm 30 forms a circular rib 33 which fits tightly by snap fit onto annular partition 26 with dual flanged circular rib 32 as shown in FIG. 2. The annular partition 26 is constructed of the same relatively rigid plastic material such as polycarbonate, polyethylene or the like, as the valve housing, while diaphragm 30 is constructed of an elastomeric material such as synthetic or natural rubber. Diaphragm 30 is of dual walled construction as shown, with the inner wall 30a having a central aperture 34 for reception of an instrument as will be described.

Figure 3:
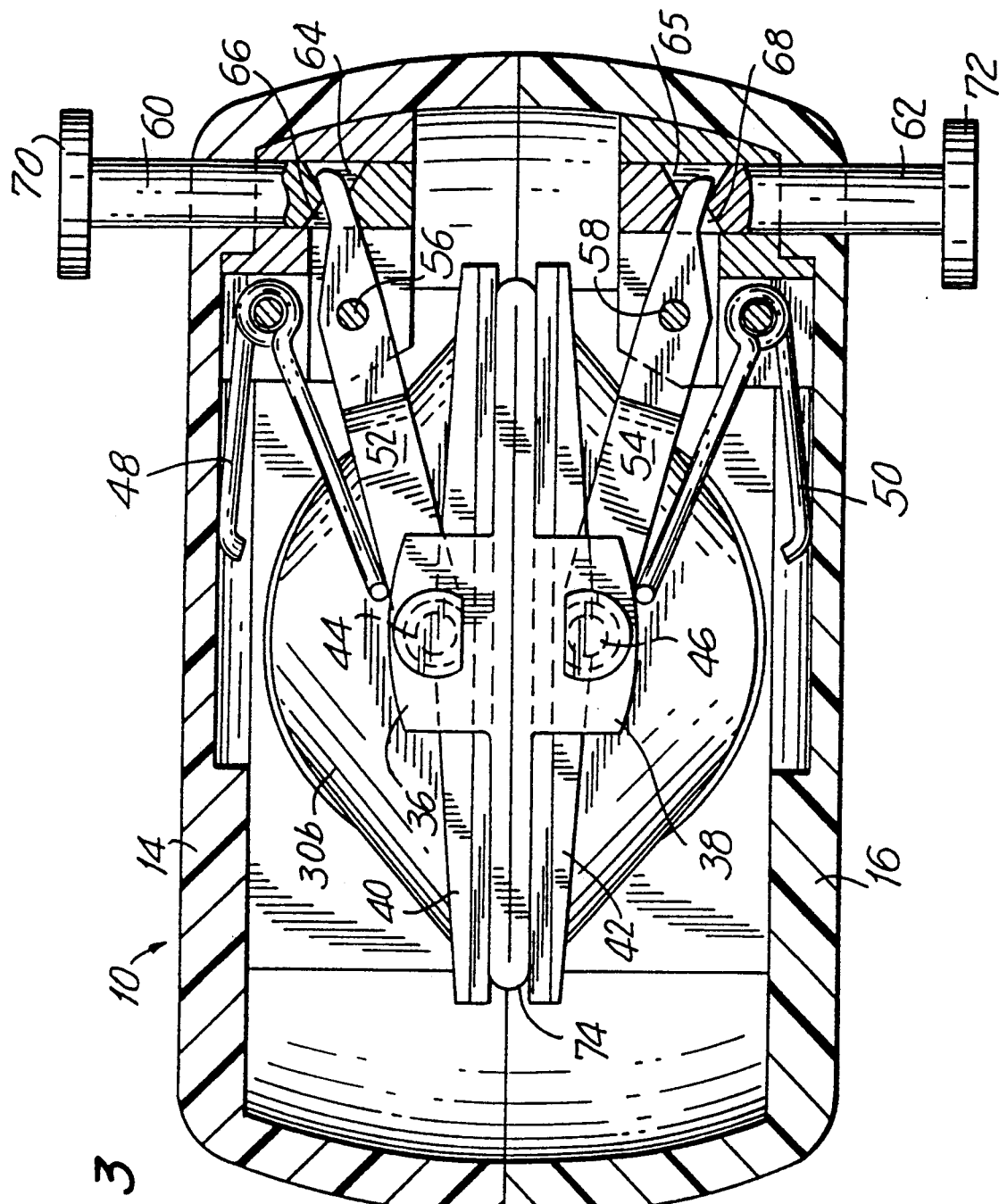
FIG. 3 is a cross-sectional view of the valve assembly of the present invention taken along lines 3—3 of FIG. 2.
Figure 4:
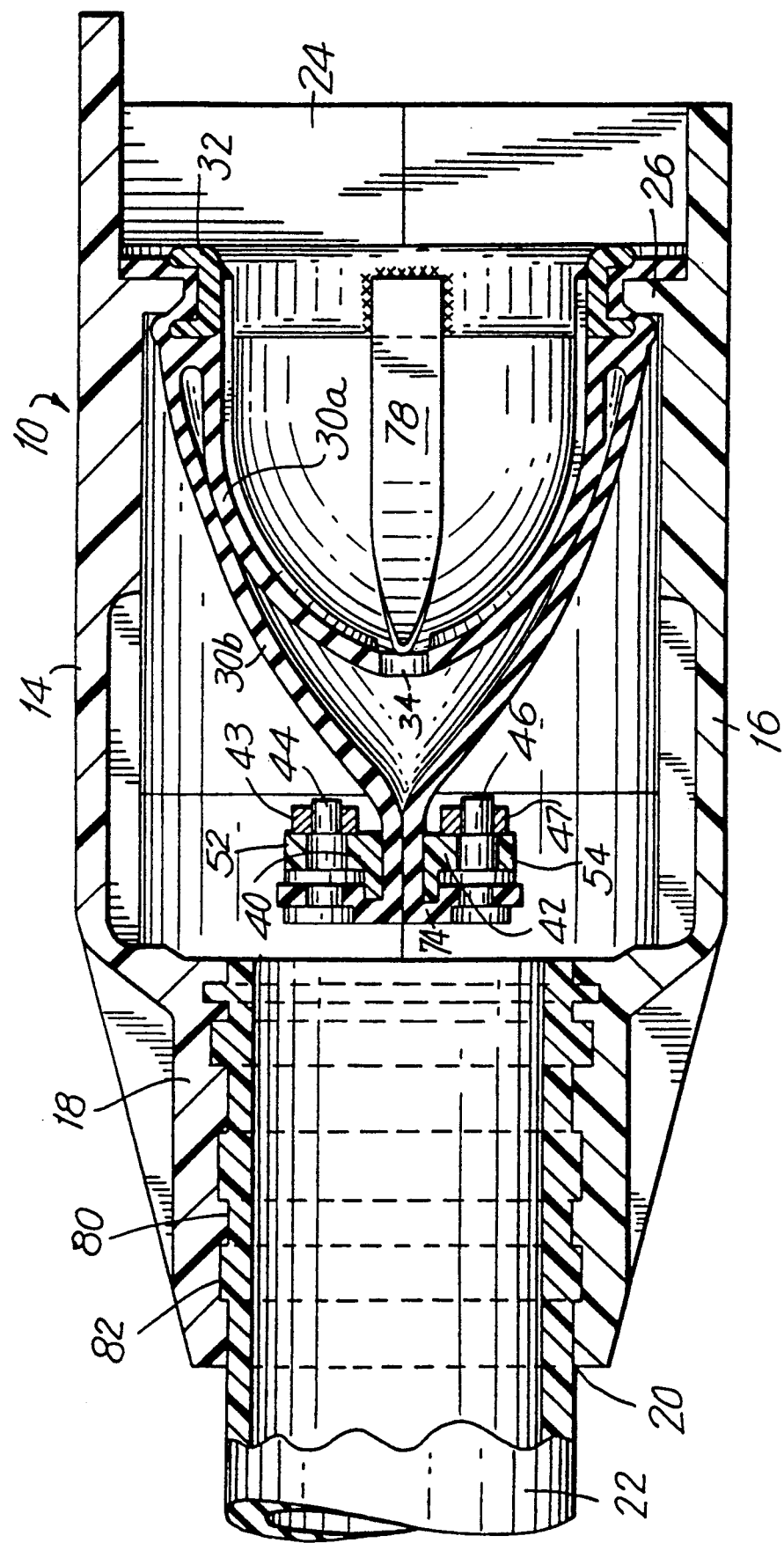
FIG. 4 is a cross-sectional view of the valve assembly of the present invention, taken along lines 4—4 of FIG. 2.

Referring now to FIG. 1 in conjunction with FIGS. 3 and 4, outer wall 30b has formed at the distal end, a pair of ears 36,38 which are connected to clamp blades 40,42 as shown, by suitable pivot pins 44,46 and attachment nuts 43,47. Each clamp blade 40,42 is biased in a direction toward the other by a torsion spring 48,50 having one leg in engagement with the adjacent housing wall and the other leg in engagement with pivotal arm 52,54 respectively pivotally mounted at pivot pin 56,58 as shown in FIG. 3. Each pivot arm 52,54 extends as shown, into the path of a pin 60,62 which is slidably mounted within elongated opening 64,65 having a circular cross-section similar to the cross-section of the pins 60,62. The inner end of each pin has an opening 66,68 for reception of the appropriate pivotal arm 52,54 such that manually depressing the slidable pins 60,62 toward each other by engagement of transverse buttons 70,72 with the thumb and index finger causes pivotal arms 52,54 to pivotally rotate arms 52,54 away from each other. This motion causes clamp blades 40,42 with ears 36,38 to separate causing outer wall 30b of dual diaphragm 30 to open at the distal end to the configuration shown in FIG. 1. When the pins 60,62 are released, the outer wall 30b of diaphragm 30 collapses to the configuration shown in FIGS. 3 and 4 under action of clamp blades 44,46 and springs 48,50, thus causing outer wall to collapse to the duckbill shape 74, providing a fluid tight seal between the proximal end of the diaphragm 30 and the distal end.

Referring now to FIG. 4 in conjunction with FIG. 1, inner elastomeric wall 30a of diaphragm 30 defines circular central aperture 34 at the distal end which is dimensioned less than or equal to the outer diameter of any instrument intended for entry into the proximal end of the valve assembly. Preferably, diaphragm 30 is fabricated from a material which is sufficiently resilient to accommodate and provide a fluid seal with instruments of varying diameters, e.g., diameters of from 5 mm to 10 mm. In FIG. 1 an endoscopic clip applying apparatus is shown at 76. However, any elongated relatively narrow instrument is contemplated.

Referring once again to FIG. 3 in conjunction with FIG. 1, diaphragm mounting and stabilizing device 31 is formed of dual flanged circular ribbed ring 32 having distally extending fingers 78 tapered at their free ends as shown. Diaphragm 30 is mounted to dual flanged circular ring 32 as shown in FIG. 4 and the entire assembly is mounted to annular partition 26 as shown. Fingers 78 are positioned within diaphragm inner wall 30a and are sufficiently flexible to conform to the shape of the inner wall while providing some degree of stability to the inner wall. Fingers 78 also assist in spreading inner wall 30a to expand aperture 34 when an instrument is inserted by distributing the spreading force more evenly. In addition to facilitating expansion of aperture 34 to conform to instrument 76, fingers 78 minimize the risk of damage to elastomeric inner wall 30a, e.g., puncture thereof, by providing an interface between the instrument 76 and the inner wall. Stabilizing device 31 is fabricated of a suitable flexible plastic material such as polyester, polypropylene, etc. and fingers 78 are preferably formed integral with dual flanged ring 32. Further, fingers 78 are sufficiently thin and flexible such that insertion into inner wall 30a of diaphragm 30 causes them to assume an initial arcuate shape as shown in FIGS. 2 and 4, similar to the generally conical shape of inner wall 30a.

Upon insertion of instrument 76 into housing opening 20 and through aperture 34 of inner wall 30a, the elastomeric material of wall 30a will expand or stretch around the instrument 76 to form a fluid tight seal. The seal is of sufficient fluid tight character that media such as pressurized gases used to insufflate a body cavity or body liquids will not pass the interface between diaphragm inner wall 30a and the instrument 76. Aperture 34, in its non-expanded or non-stretched condition, is typically approximately 3 to 15 mm to accommodate elongated endoscopic instruments while maintaining sufficient sealed contact with the other surface thereof. However, such dimensions will vary depending upon the size of the instruments and the intended application. Further, manipulation of the instrument in any direction will not affect the seal, since the elastomeric material will remain in tight contact with the outer surface of the instrument.

At the point when the instrument 76 has passed the inner wall 30a and entered aperture 34, a gas tight seal has been created between the instrument and the inner wall 30a. The surgeon then squeezes pins 60,62 with the thumb and index finger causing the distal end of outer wall 30b of diaphragm 30 to expand to the shape shown in FIG. 1 thus permitting continued entry of the instrument 76 through the entire valve body housing 15 and into the cannula 22. Depending upon the particular procedure, the surgeon may prefer to squeeze pins 60,62 thereby opening outer wall 30b prior to entry of instrument 76 into the valve housing 15 and into diaphragm inner wall 30a.

Cannula 22 is connected to the distal end of the valve housing at neck 18 which has a series of alternating circular shaped ribs 80 and valleys 82. Cannula 22 is fabricated of a rigid material such as a plastic, fiberglass or metal and is supported in position as shown in FIGS. 2 and 4 within neck 18 by the ribs 80 which are formed of the same material. Alternatively, the tube 22 may be of elastomeric material in which case it would simply be flexible and resilient so as to be assembled with distal neck 18 by inserting the tube into the neck and distorting the outer shape until it is snapped into position as shown within ribs 80.

The operation of the valve assembly will now be described. The valve assembly is intended to be supplied as part of a cannula assembly, i.e. a valve assembly with distal cannula tube 22 positioned as shown. A trocar is a sharp pointed instrument usually fitted within a cannula assembly and used to insert the cannula into a body cavity by first piercing an aperture in the cavity wall (i.e., the peritoneum). The cannula is then inserted into the punctured body wall of the patient. Thereafter, the trocar is removed, permitting insertion of instruments into the patient's body through the cannula to perform the desired procedure. Thus, the significance of providing control to the surgeon of the sealed state of the opening in the cannula assembly cannot be overemphasized. Such opening will ultimately control the exposure between the internal part of the body cavity and the outside atmosphere. For laparoscopic procedures the valve assembly will preserve the state of insufflation of the peritoneum during the surgical procedures.

The surgeon removes the trocar from the cannula assembly thereby permitting the opening of outer wall 30b of diaphragm 30 to close automatically under the action of springs 48,50. Thereafter, the surgeon inserts an instrument into the body cavity by first inserting it into the proximal end of the valve assembly, through dual flanged ring 32 and then through aperture 34 of inner diaphragm wall 30a. Pins 60,62 may be selectively squeezed as desired by the surgeon to open the distal end of outer wall 30b to permit entry of the instrument into cannula 22 and into the body cavity. At this point, the tight contact between the instrument 76 and the diaphragm inner wall 30a at aperture 34 has sealed the inner body cavity from the outside atmosphere. This seal is provided by the resilient property of the stretched elastomeric material surrounding opening 34. Thus, separating clamp plates 40,42 to open outer diaphragm wall 30b to permit entry of instrument 76 into cannula 22 does not affect the sealed condition of the inner anatomical cavity. As noted previously, manipulation of the instrument in any direction will not affect the seal, since the elastomeric material defining the opening 34 will conform to the movements of the instrument and assume an elliptical or other shape necessary to maintain contact.

As noted, aperture 34 is preferably dimensioned between 3 and 15 mm to accommodate laparoscopic and endoscopic instruments such as clip appliers, laser tubes, photographic instruments, tubes or the like. However, depending upon need or application this dimensional range may be varied to accommodate any particular instrument.

The opening at the distal end of outer wall 30b is always under the surgeon's control through pins 60,62 and is adapted to be automatically actuated to the closed duckbill shaped position 74 under action of springs 48,50 when the surgeon removes the instrument 76 or other object from the valve assembly. Further, manipulation of the instrument 76 does not affect the shape of aperture 34 or the sealing contact of inner wall 30 or with the instruments because diaphragm 30 is sufficiently flexible and resilient to maintain contact with the surface of the instrument 76. Thus, during the entire sequence the integrity of the seal between the inside of the body cavity and the outside atmosphere is clearly maintained at all times.

We claim:
1. Valve assembly for sealed reception of an elongated object, which comprises:
   a) valve body defining a longitudinal axis and having at least one opening configured and dimensioned to permit entry of the elongated object;
   b) flexible resilient valve member defining an aperture positioned in general alignment with said at least one opening; and
   c) means associated with said flexible resilient valve member to facilitate expansion of said aperture to permit entry of the elongated object therethrough in sealed engagement therewith, said means to facilitate expansion of said aperture adapted for radial displacement relative to said longitudinal axis and positioned to expand said aperture upon contact with the elongated object as the elongated object is at least partially inserted into said at least one opening of said valve body.

2. Valve assembly according to claim 1 wherein said resilient valve member is adapted to engage and conform to the outer surface of the elongated object in substantially fluid tight manner.

3. Valve assembly for sealed reception of an elongated object, which comprises:
   a) valve body having means configured and dimensioned to permit entry of the elongated object;
   b) flexible resilient valve means defining an aperture positioned in general alignment with said entry means; and
   c) relatively rigid means associated with said resilient valve means and having portions adapted to be displaced relative to a central axis defined by said valve body upon contact with the elongated object as the elongated object is at least partially inserted into said entry means of said valve body, said portions positioned and dimensioned to expand said aperture to permit entry of the elongated object therethrough during displacement of said portions.

4. Valve assembly according to claim 3 further comprising secondary valve means positioned adjacent said flexible resilient valve means and in general alignment therewith, said secondary valve means movable between a first position which blocks entry of the elongated object and a second position which permits entry of the elongated object.

5. Valve assembly according to claim 4 wherein said secondary valve means comprises at least one member movable toward and away with respect to a rigid member to respectively assume said first and second positions.

6. Valve assembly according to claim 5 comprising resilient means to bias said at least one member toward said rigid member.

7. Valve assembly according to claim 6 wherein said at least one member is adapted to provide a substantially fluid tight seal when in said first position.

8. Valve assembly according to claim 7 wherein said at least one member is pivotal between said first and second positions.

9. Valve assembly according to claim 5 wherein said valve body is a rigid housing.

10. Valve assembly according to claim 9 wherein said valve body is a trocar housing.

11. Valve assembly according to claim 10 wherein the elongated object is a trocar.

12. Valve assembly for introduction of an elongated object into a patient's body, which comprises:
   a) valve body member defining a proximal inlet opening and a distal outlet opening;
   b) first valve member formed of a flexible elastomeric resilient material and defining an aperture for reception of the elongated object, said aperture being configured and dimensioned such that insertion of the elongated object into said aperture causes said flexible resilient material defining said aperture to resiliently engage and conform to an outer surface portion of the elongated object in substantially fluid tight manner;
   c) second valve member positioned adjacent said first valve member and in general alignment therewith, said second valve member defining an aperture in general alignment with said aperture of said first valve member, and being formed of a flexible resilient material at least in the region adjacent to and defining said aperture; and
   d) means engageable with the elongated object upon insertion thereof into said proximal inlet opening of said valve body member, and adapted to be radially displaced relative to a central axis defined by said valve body member to facilitate expansion of said aperture of said first valve member to facilitate entry of the object therein.

13. The valve assembly according to claim 12 wherein said first and second valve members are formed integral of a flexible elastomeric resilient material, said first valve member connected to said second valve member at the proximal end thereof, said first valve member being positioned at least partially within said second valve member.

14. Valve assembly according to claim 13 wherein said proximal end of said first and second valve members is attached to and supported by an annular ring.

15. Valve assembly according to claim 14 wherein said means engageable with the elongated object comprises a plurality of elongated resilient fingers associated with said valve body, said resilient fingers positioned within said first valve member in supporting contact with inner surface portions thereof and engageable with the elongated object upon at least partial insertion of the elongated object into said proximal inlet opening of said valve body member, said fingers adapted for radial displacement relative to a longitudinal axis defined by said annular ring upon engagement with the elongated object to radially expand said aperture of said first valve member to facilitate entry of the elongated object.

16. Valve assembly according to claim 15 wherein said annular ring member comprises a flexible plastic material selected from the group consisting of polyester and polypropylene and said plurality of elongated resilient fingers associated with said valve body are integral with said annular ring.

17. Valve assembly according to claim 16 wherein said means engageable with the elongated object comprises four of said flexible fingers.

18. Valve assembly according to claim 12 further comprising manually operable means for selectively opening said aperture of said second valve member whereby the object may pass therethrough.

19. Valve assembly adapted for introduction of an elongated object into a patient's body, which comprises:
   a) first valve means formed of a resilient material and defining an aperture for reception of the elongated object, said aperture being configured and dimensioned such that insertion of the elongated object into said aperture will cause the resilient material defining said aperture to resiliently engage the outer surface of the elongated object in substantially fluid tight manner;
   b) second valve means positioned adjacent said first valve means in general alignment therewith, said second valve means defining an aperture in general alignment with said aperture of said first valve means, and being formed of a flexible material at least in the region defining said aperture;
   c) means associated with said first valve means and engageable with the elongated object as the elongated object is at least partially inserted into said aperture of said first valve means, and adapted to be radially displaced to facilitate expansion of said aperture of said first valve means during introduction of the elongated object within the valve assembly; and
   d) manually operable means to selectively permit said aperture of said second valve means to be opened or closed so as to permit entry of the elongated object.

20. Valve assembly adapted for introduction of an elongated object into a patient's body, which comprises:
   a) first valve means formed of a resilient material and defining an aperture for reception of the elongated object, said aperture being configured and dimensioned such that insertion of the elongated object into said aperture will cause the resilient material defining said aperture to resiliently engage the outer surface of the elongated object in substantially fluid tight manner;

b) second valve means positioned adjacent said first valve means in general alignment therewith, said second valve means defining an aperture in general alignment with said aperture of said first valve means, and being formed of a flexible material at least in the region defining said aperture;

c) a plurality of distally extending resilient flexible fingers formed integral with a valve support ring and positioned within said first valve means in supporting contact with inner surface portions thereof, said fingers configured and dimensioned to engage the elongated object during introduction of the elongated object within the valve assembly, whereby engagement of the elongated object by said resilient fingers causes radial displacement of said fingers relative to a longitudinal axis defined by said support ring so as to cause radial expansion of said aperture of said first valve means to facilitate entry of the elongated object.

21. Valve assembly for sealed reception of an elongated object, which comprises:

a) valve body defining at least one opening configured and dimensioned to permit entry of the elongated object;

b) flexible resilient valve member defining an aperture positioned in general alignment with said at least one opening in said valve body; and c) at least two relatively rigid members associated with said valve member and engageable with the elongated object upon introduction into said at least one opening of said valve body, and adapted to be radially displaced relative to a central axis of said valve body to facilitate expansion of said aperture of said resilient valve member prior to entry of the elongated object into said aperture.

22. Valve assembly for sealed reception of an elongated object into a patient's body, which comprises:

a) valve body defining a first inlet opening and a second outlet opening;

b) flexible resilient valve member defining an aperture positioned in general alignment with at least said first inlet opening for reception of the elongated object, said aperture being configured and dimensioned such that insertion of the elongated object into said aperture will cause the flexible resilient material defining said aperture to resiliently engage and conform to the outer surface of the elongated object in a substantially fluid tight manner; and c) means engageable with the elongated object upon insertion thereof into said first inlet opening and adapted to be displaced away from a central axis defined by said valve body to expand said aperture of said resilient valve member to facilitate entry of the elongated object therein.

23. Valve assembly according to claim 22 wherein said means engageable with the elongated object comprises valve support means, said valve support means being adapted to support said resilient valve member and including a support ring having at least two distally extending resilient flexible fingers positioned within said resilient valve member in supporting contact with the inner surface thereof, whereby engagement of the elongated object by said at least two resilient fingers causes radial displacement of said fingers relative to a longitudinal axis defined by said support ring so as to cause radial expansion of said aperture of said resilient valve member to facilitate entry of the elongated object.

24. Valve assembly according to claim 23 wherein each said flexible finger has a proximal end portion and a distal end portion, each said distal end portion of said flexible fingers being disposed radially inwardly of said corresponding proximal end portion.

25. Valve assembly according to claim 24 wherein said distal end portions of said flexible fingers are each generally angularly displaced relative to said longitudinal axis defined by said support ring.

26. Valve assembly for sealed reception of an elongated object, which comprises:

a) valve body defining a generally longitudinal axis and having at least one opening configured and dimensioned to permit entry of the object;

flexible resilient valve member positioned within said valve body and defining an aperture positioned in general alignment with said at least one opening of said valve body; and c) at least two projecting members associated with said flexible resilient valve member and extending in a generally distal direction, each said at least two projecting members having at least a portion thereof adapted to move generally radially to facilitate expansion of said aperture to permit entry of the elongated object therethrough in sealed engagement therewith.

27. Valve assembly according to claim 26 wherein each said projecting member has a proximal end portion and a distal end portion which is disposed generally radially inward of said corresponding proximal end portion.

28. Valve assembly according to claim 27 wherein portions of said at least two projecting members adapted to move radially to facilitate said expansion of said aperture are located at the distal end portions of said projecting members.

29. Valve assembly according to claim 28 wherein each said distal end portion of said projecting members is generally oriented at an angle relative to said longitudinal axis.

30. Valve assembly according to claim 29 wherein said at least two projecting members contact at least a portion of said resilient valve member and are positioned for engagement with the elongated object upon insertion thereof into said at least one opening of said valve body, at least portions of said at least two projecting members adapted for generally radial displacement relative to said longitudinal axis upon engagement by the elongated object to cause radial expansion of said aperture.

31. Valve assembly according to claim 30 wherein said projecting members are attached to an annular ring.

32. Valve assembly according to claim 31 wherein said annular ring comprises a material selected from the group consisting of polyester and polypropylene, said projecting members being integrally formed with said annular ring.

33. Valve assembly according to claim 32 wherein said projecting members are monolithically formed with said annular ring.

34. Valve assembly according to claim 33 wherein at least four of said projecting members are provided.

35. Valve assembly for sealed reception of an elongated object, which comprises:

a) valve body defining an inlet opening configured and dimensioned to permit entry of the elongated object;

b) flexible resilient valve member defining an aperture positioned in general alignment with said inlet opening; and
c) at least one relatively rigid member having at least a portion thereof adapted to be displaced radially relative to a central axis defined by said valve body, said at least a portion of said at least one relatively rigid member positioned and dimensioned to expand said aperture of said flexible resilient valve member upon contact with the elongated object as the elongated object is at least partially inserted into said inlet opening.

36. Valve assembly according to claim 35 comprising at least two said relatively rigid members.

37. Valve assembly according to claim 35 comprising at least four said relatively rigid members.

* * * * *

UNITED STATES PATENT AND TRADEMARK OFFICE
CERTIFICATE OF CORRECTION

PATENT NO. : 5,304,143
DATED : April 19, 1994
INVENTOR(S) : David T. Green, et al It is certified that error appears in the above-indentified patent and that said Letters Patent is hereby corrected as shown below:

On the title page, Item [75] Inventor: should read --David T. Green, Westport; Henry Bolanos, East Norwalk; Henry Sienkiewicz; all of Connecticut--

Signed and Sealed this

Second Day of August, 1994

Attest:

BRUCE LEHMAN

Attesting Officer

Commissioner of Patents and Trademarks